United States Patent [19]

Rule et al.

[11] Patent Number: 4,935,559
[45] Date of Patent: Jun. 19, 1990

[54] OLEFINATION OF IODOAROMATIC COMPOUNDS

[75] Inventors: Mark Rule, Kingsport; Eric J. Fugate, Jonesborough, both of Tenn.

[73] Assignee: Eastman Kodak Company, Rochester, N.Y.

[21] Appl. No.: 303,347

[22] Filed: Jan. 30, 1989

Related U.S. Application Data

[63] Continuation-in-part of Ser. No. 167,930, Mar. 14, 1988, abandoned.

[51] Int. Cl.$^5$ ........................ C07C 17/00; C07C 1/253
[52] U.S. Cl. .................................... 570/181; 585/436; 585/438

[58] Field of Search ................. 570/181; 585/436, 438

[56] References Cited

PUBLICATIONS

Mori, K. Bulletin Chem. Soc. Jap 46(5) 1505–1508 1973.

*Primary Examiner*—Paul J. Killos
*Attorney, Agent, or Firm*—Charles R. Martin; William P. Heath, Jr.

[57] ABSTRACT

A method of preparing an aryl alkene compound comprising reacting an iodoaromatic compound an alkene and an alkanol in the presence of a palladium catalyst and the absence of a Bronsted base.

10 Claims, No Drawings

OLEFINATION OF IODOAROMATIC COMPOUNDS

This application is a continuation-in-part of Ser. No. 167,930 filed Mar. 14, 1988 now abandoned.

The present invention relates to a novel process for preparing aryl alkylene compounds by reacting an iodoaryl compound with an alkene and an alkanol in the presence of a noble metal catalyst.

It is known that iodoaromatic compounds will undergo a vinylic substitution reaction with an alkene in the presence of a basic tertiary amine or sodium acetate and a palladium metal catalyst to produce aryl alkene compounds (R. F. Heck and J. P. Nolley, Jr., *Org. Chem.*, 37, 2320 (1972) and T. Mizorski, K. Mori and A. Ozaki, *Bull. Chem. Soc. Japan,* 44, 581 (1971)). Also, U.S. Pat. No. 3,922,299 to Heck discloses producing aryl alkene compounds by reacting an iodoaromatic compound, an alkene, a basic tertiary amine, and an organic trivalent arsenic compound or an organic trivalent phosphorus compound, in the presence of a palladium acetate catalyst. The primary function of the basic tertiary amine in the above references is to neutralize iodide removed from the iodoaromatic compound. Unlike the above references, the instant invention utilizes an alkanol instead of a basic compound, such as a tertiary amine, to neutralize the iodide. An important advantage of the instant invention is that the iodoalkane species that are formed are easily separated from the reaction products and the iodine is more easily recovered. Further, the instant invention does not require the presence of a trivalent arsenic or phosphorus compound as disclosed by the Heck patent.

In summary this invention is a process for obtaining aryl alkene compounds comprising reacting an iodoaromatic compound with an alkene and an alkanol in the absence of a Bronsted base and in the presence of a palladium catalyst.

The iodoaryl reactants can be monoiodoaromatic compounds and diiodoaromatic compounds. Examples of suitable iodoaryl compounds are iodine substituted benzene derivatives such as iodobenzene, 1,4-diiodobenzene, 1,3-diiodobenzene, methyl-p-iodobenzoate, iodoanisole and the like and iodine substituted naphthalene compounds such as iodonaphthalene. Monoiodobenzene is preferred.

The alkene can be an alpha-olefin of at least 2 carbon atoms up to be about 10 carbon atoms or more. The preferred alkenes are the alpha-olefins of 2–6 carbon atoms such as ethylene, propylene, 1-butylene, isobutylene, 1-pentene, 1-hexene and the like. The alkene reactant particularly preferred is ethylene.

The alkanol reactant of the invention can be any alkanol of at least 1 carbon atom, preferably up to 12 carbon atoms. Examples of suitable alkanols include methanol, ethanol, butanol, pentanol and the like. The alkanol reactant most preferred is methanol.

The catalyst comprises palladium metal free or supported, or any palladium salt or complex. Examples of suitable catalysts include palladium iodide, palladium nitrate, palladium sulfate, palladium acetate, palladium tetrakis (triphenyl phosphine), palladium bis(2,4-pentanedione), palladium on alumina, or palladium on carbon. The preferred catalysts are palladium salts or finely divided metal. Particularly preferred is palladium acetate.

In the process of the instant invention, the reactants must be present in at least stoichiometric quantities based on the amount of iodoaromatic compound present in the reaction mixture. Preferably the alkanol and/or the alkene are present in excess to improve the yield of the desired product. The catalyst is employed in catalytic amounts, preferably ranging from about 0.05 wt. % to 5.0 wt. % based on the weight of iodoaromatic reactant.

The reaction may be carried out at a temperature of about 125°–225°, preferably 150°–200° C.

The reaction can be conveniently effected under atmospheric pressure but pressures higher than atmospheric can be employed if desired.

The first step of reacting the iodoaromatic compound, alkene and alkanol is conducted in the absence of a Bronsted base. By the term "Bronsted base" we mean any compound or radical other than the alkyl portion of the alkanol which combines with hydrogen iodide to form an ionic iodide-containing salt. For example reactions are known in the prior art where potassium acetate is used to provide a moiety to which hydrogen iodide can bond. Other metal compounds such as lithium acetate, lithium hydroxide, lithium methoxide, sodium acetate, sodium benzoate, potassium hydroxide, calcium oxide, and calcium acetate can also be used. Other Bronsted bases are basic primary, secondary and tertiary amines, such as methyl amine, dimethyl amine, trimethyl amine, triethyl amine, tributyl amine, and trioctyl amine. Still other Bronsted bases are tributyl phosphine and tricyclohexyl phosphine.

The absence of the Bronsted base is a critical aspect of this invention. Due to the cost of the iodine substantially all of the iodine must be recovered in a commercially acceptable process. When the Bronsted bases of the prior art are used the iodine is very difficult to recover because it is in the form of a water-soluble, nonvolatile salt. In the present invention the iodine is bonded to the alkyl portion of the alkanol forming an alkyl iodide from which the iodine can be economically recovered.

The desired product of the instant process is an aryl alkene compound in which the alkene group(s) correspond to the alkene reactant. The product can be either a monoalkene aryl compound or a polyalkene aryl compound such as a diaryl alkene compound. Examples of compounds formed by the invention include styrene, 1,4-divinylbenzene, 1,3-divinylbenzene, 1-vinyl naphthalene, methyl-p-vinylbenzoate and the like. Since the preferred aryl alkene compound in iodobenzene and the preferred alkene compound is ethylene the preferred aryl alkene is styrene.

A by-product of the present invention is the corresponding alkoxyalkyl aromatic, which can be converted to the desired aryl alkene by known methods.

The desired aryl alkene product can be separated from unreacted iodoaromatic compound, alkyl iodide and the alkanol by known methods including those taking advantage of the different vapor pressure boiling points of these compounds, e.g., distillation. The separated alkanol can be reused in another reaction mixture and the separated alkyl iodide can be dehalogenated by methods known in the art to allow for the recovery of iodine.

EXAMPLES

In the examples below, the stated amounts of reactants and catalyst were placed in an autoclave and subjected to the conditions described. No Bronsted base was present. The reaction product was analyzed by gas chromatography. The results have been confirmed by GC-mass spectroscopy and are reported in terms of mole percent, based on the moles of iodoaromatic compound.

| Example 1 | |
|---|---|
| Reactants - | 100 mL methanol |
| | 10 g iodobenzene |
| | 1000 psig ethylene |
| Catalyst - | 0.02 g palladium acetate |
| Temperature - | 200° C. |
| Time - | 2 hours |
| products - | 20.2% styrene; |
| | 78.1% of iodobenzene |
| | 1.4 g of methyl iodide |

| Example 2 | |
|---|---|
| Reactants - | 100 mL methanol |
| | 10 g iodobenzene |
| | 500 psig ethylene |
| Catalyst - | 0.02 g palladium acetate |
| Temperature - | 200° C. |
| Time - | 2 hours |
| Products - | 42.0% styrene; |
| | 38.1% of iodobenzene |
| | 2.9 g of methyl iodide |

| Example 3 | |
|---|---|
| Reactants - | 100 mL methanol |
| | 5 g 1,4-diiodobenzene |
| | 500 psig ethylene |
| Catalyst - | 0.05 g palladium acetate |
| Temperature - | 150° C. |
| Time - | 3 hours |
| Products - | 21.6% 1,4-divinylbenzene |
| | 33.9% 1-vinyl,4-(alpha-methoxyethyl)benzene |
| | 11.8% 4-vinyl iodobenzene |
| | 15.1% 1,4-(alpha-methoxyethyl)benzene |
| | 2.4% 4-(alpha-methoxyethyl)iodobenzene |
| | 15.5% 1,4-diiodobenzene |
| | 3.3 g methyl iodide |

| Example 4 | |
|---|---|
| Reactants - | 100 mL methanol |
| | 5 g 1,3-diiodobenzene |
| | 500 psig ethylene |
| Catalyst - | 0.05 g palladium acetate |
| Temperature - | 150° C. |
| Time - | 3 hours |
| Products - | 42.1% 1,3-divinylbenzene |
| | 30.1% 1-vinyl,3-(alpha-methoxyethyl)benzene |
| | 9.5% 3-vinyl iodobenzene |
| | 7.0% 1,3-(alpha-methoxyethyl)benzene |
| | 1.1% 3-(alpha-methoxyethyl)iodobenzene |
| | 8.7% 1,3-diiodobenzene |
| | 3.6 g methyl iodide |

| Example 5 | |
|---|---|
| Reactants - | 100 mL methanol |
| | 5 g 1-iodonaphthalene |
| | 500 psig ethylene |
| Catalyst - | 0.05 g palladium acetate |
| Temperature - | 150° C. |
| Time - | 3 hours |
| Products - | 37.6% 1-vinyl naphthalene |
| | 20.0% 1-(alpha-methoxyethyl)naphthalene |
| | 42.5% 1-iodonaphthalene |
| | 1.6 g methyl iodide |

| Example 6 | |
|---|---|
| Reactants - | 100 mL methanol |
| | 5 g methyl-p-iodobenzoate |
| | 500 psig ethylene |
| Catalyst - | 0.05 g palladium acetate |
| Temperature - | 150° C. |
| Time - | 3 hours |
| Products - | 89.1% methyl-p-vinylbenzoate |
| | 1.1% methyl-p-(alpha-mehoxyethyl)benzoate |
| | 9.8% methyl-p-iodobenzoate |
| | 2.4 g methyl iodide |

| Example 7 | |
|---|---|
| Reactants - | 100 mL methanol |
| | 5.6 g 4-iodoanisole |
| | 500 psig ethylene |
| Catalyst - | 0.05 g palladium acetate |
| Temperature - | 150° C. |
| Time - | 3 hours |
| Products - | 9.4% 1-vinyl,4-methoxybenzene |
| | 37.7% 1-(alpha-methoxyethyl)4-methoxybenzene |
| | 15.2% 4-iodoanisole |
| | 37.3% p,p'-dimethoxy stilbene |
| | 2.8 g methyl iodide |

We claim:
1. A process comprising
(a) preparing an aryl alkene compound and an alkyl iodide by reacting an iodoaromatic compound and an alkene and an alkanol in the presence of a palladium catalyst and in the absence of any compound or radical other than the alkyl portion of the alkanol which combines with hydrogen iodide to form an ionic iodine-containing salt,
(b) recovering the alkyl iodide.
2. The method of claim 1 wherein the palladium is a palladium salt.
3. The method of claim 2 wherein the palladium salt is palladium acetate.
4. The method of claim 1 wherein the alkanol is a $(C_1-C_{12})$ alkanol.
5. The method of claim 1 wherein the $(C_1-C_{12})$ alkanol is methanol.
6. The method of claim 1 wherein the temperature is in the range of about 125° C. to about 225° C.
7. The method of claim 1 wherein the iodoaromatic compound is a monoiodoaromatic compound.
8. The method of claim 1 wherein the monoiodoaromatic compound is iodobenzene.
9. The method of claim 1 where the alkene is ethylene.
10. A process comprising
(a) preparing styrene and methyl iodide by reacting at a temperature of 125° C. to 225° C. iodobenzene, ethylene and methanol in the presence of palladium acetate and in the absence of any compound or radical other than the alkyl portion of the alkanol which combines with hydrogen iodide to form an ionic iodine-containing salt, and
(b) recovering the methyl iodide.

* * * * *